United States Patent [19]

Chevallet

[11] Patent Number: 5,644,402

[45] Date of Patent: Jul. 1, 1997

[54] DEVICE FOR DETECTING A CONDUIT AND FOR DETERMINING AT LEAST ONE CHARACTERISTIC OF ITS CONTENT

[75] Inventor: Jacques Chevallet, Serezin Du Rhone, France

[73] Assignee: Hospal Industrie, France

[21] Appl. No.: 457,219

[22] Filed: Jun. 1, 1995

[30] Foreign Application Priority Data

Oct. 7, 1994 [FR] France ................... 94 12252

[51] Int. Cl.$^6$ ................................................. G01N 21/85
[52] U.S. Cl. .................. 356/440; 250/559.4; 250/576; 356/410
[58] Field of Search ...................... 356/410, 440; 250/576, 577, 559.4

[56] References Cited

U.S. PATENT DOCUMENTS

| | | | |
|---|---|---|---|
| 3,908,441 | 9/1975 | Virloget | 250/577 X |
| 3,999,861 | 12/1976 | Bellinger | 356/410 |
| 4,114,144 | 9/1978 | Hyman | 340/632 |
| 4,297,588 | 10/1981 | Hastbacka | 250/577 |
| 4,366,384 | 12/1982 | Jensen | 250/575 |
| 4,477,186 | 10/1984 | Carlson | 356/246 |
| 4,857,050 | 8/1989 | Lentz et al. | 604/67 |
| 5,261,874 | 11/1993 | Castle | 604/4 |

FOREIGN PATENT DOCUMENTS

| | | | |
|---|---|---|---|
| 199904A | 11/1986 | European Pat. Off. | |
| 2660755 | 10/1991 | France | |
| 3910250 | 10/1990 | Germany | |
| 60-140141 | 7/1985 | Japan | 356/440 |

Primary Examiner—Vincent P. McGraw
Attorney, Agent, or Firm—Finnegan, Henderson, Farabow, Garrett & Dunner, L.L.P.

[57] ABSTRACT

A device for detecting a conduit and for determining at least one characteristic of its content includes a seat for housing at least a portion of the conduit. The seat has first and second zones which are opposite each other with respect to a recess intended to receive the conduit. A light emitter is arranged in the first zone, and has a preferential emission direction oriented towards the recess. A receptor sensitive to the light emitted by the emitter also has a preferential reception direction oriented towards the recess. A first deflector deflects light in the direction of the first zone when a conduit containing a substantially transparent liquid is engaged in the seat. A second deflector deflects in the direction of the second zone at least part of the light deflected by the first deflector so that, when a conduit containing a substantially transparent liquid is engaged in the seat, at least part of the light emitted by the emitter reaches the receptor after having passed through the conduit at least twice obliquely with respect to a longitudinal axis of the recess. The components are arranged so that in the absence of a conduit in the seat, at least part of light from the emitter reaches the receptor after a single deflection.

12 Claims, 2 Drawing Sheets

DEVICE FOR DETECTING A CONDUIT AND FOR DETERMINING AT LEAST ONE CHARACTERISTIC OF ITS CONTENT

BACKGROUND OF THE INVENTION

1. Field of the Invention

The subject of the present invention is a device for detecting a conduit and for determining at least one characteristic of its content.

2. Description of the Related Art

In all apparatuses for treating blood by means of extracorporeal circulation, in which the patient's blood is circulated in a semipermeable-membrane exchanger (dialyser, filter for plasmapheresis or haemofiltration for example), it is important to be able to check during treatment, in a continuous manner, that the membrane of the exchanger has not suffered rupture, especially due to the effect of the transmembrane pressure created in the exchanger in order to cause plasmatic liquid to pass through the membrane from the blood compartment of the exchanger to the spent-liquid compartment.

A means commonly used for checking the integrity of the membrane of the exchangers used for the purposes which have just been mentioned consists in placing, on an outlet line from the spent-liquid compartment of the exchanger, a blood detection device in the liquid flowing in the line. Generally, these detection devices are also provided in order to detect the presence of the line, whatever its content (air or saline solution), as a sine qua non condition of operation.

German Patent 3 910 250 describes a detector of this type, comprising:

- a seat for housing a first line portion, comprising a first and a second zone which are opposite each other with respect to the longitudinal axis of the line when it is housed in the seat;
- light emission means and reception means sensitive to the light emitted by the emission means, the emission means and the reception means being arranged in the first zone in order to have parallel emission and reception directions; and
- light deflection means arranged in the second zone in order to send back towards the reception means at least part of the light emitted by the emission means.

In the embodiments described, the deflection means are formed by two mirrors arranged so as to face each other and respectively making an angle of 45° with respect to the emission direction and the reception direction. The light emitted by the emission means is reflected twice before reaching the reception means and the optical path between the emission and reception means is always the same, whether or not a line has been engaged in the seat, and whatever the nature of the fluid present in the line (gas or liquid). With this device, a difference in nature or in quality of the fluid present in the line (liquid or gas, liquid containing or not containing blood) is manifested, within the sensitivity limit of the reception means and of the signal processing circuit with which it is associated, by a different attenuation of the light emitted by the emission means in the region of the reception means.

SUMMARY OF THE INVENTION

An object of the invention is to produce a detection device of the type mentioned hereinabove which has an increased capacity for discriminating between fluids of various kinds or of various quality and which furthermore is suitable for detecting very small quantities of blood in a liquid flowing in a line of very small diameter.

In order to achieve this object, a device is provided, according to the invention, for detecting a conduit and for determining at least one characteristic of its content, comprising:

- a seat for housing at least one portion of the conduit, comprising a first and a second zone which are opposite each other with respect to a recess intended to receive the conduit;
- light emission means, arranged in the first zone, having a preferential emission direction oriented towards the recess and reception means, sensitive to the light emitted by the emission means, having a preferential reception direction oriented towards the recess; and
- first light deflection means for deflecting, in the direction of the first zone, at least part of the light emitted by the emission means, at least when a conduit containing a substantially transparent liquid is engaged in the seat;
- second light deflection means for deflecting, in the direction of the second zone, at least part of the light deflected by the first deflection means so that, when a conduit containing a substantially transparent liquid is engaged in the seat, at least part of the light emitted by the emission means reaches the reception means after having passed through the conduit at least twice obliquely with respect to a longitudinal axis of the recess.

This device has a double advantage related to the multiple deflections forcing at least part of the light emitted by the emission means to pass obliquely through the conduit several times. On the one hand, by virtue of the elongation of the optical path inside the conduit, it is possible to detect blood concentrations in a spent liquid which are much lower than with conventional devices, or in conduits of much smaller cross-section. On the other hand, the obliquity, with respect to several media of different refractive index arranged in parallel layers, of portions of multiple optical paths, makes it possible to arrange the emission means, the reception means and the first and second deflection means with respect to each other so that the discrimination between the various detection situations (presence or absence of a conduit in the seat, nature of the fluid in the conduit) can be performed in a more clear-cut manner. Thus, in one embodiment of the invention, the emission means, the reception means and the first and second deflection means are arranged so that:

- in the absence of a conduit in the seat, at least part of the light emitted by the emission means reaches the reception means after a single deflection;
- when a conduit containing a gas is engaged in the seat, the reception means receive practically no light coming from the emission means; and
- when a conduit containing a substantially transparent liquid is engaged in the seat, at least part of the light emitted by the emission means reaches the reception means after having passed through the conduit four times.

According to one characteristic of the invention, the device is used as a blood detector in a spent-liquid line of an apparatus for treating blood by means of extracorporeal circulation, and the wavelength of the light emitted by the emission means is chosen to be outside the spectrum of visible light and not to be absorbed by a liquid having the coloration of a blood ultrafiltrate possibly diluted in a saline solution.

By virtue of this arrangement, the attenuation of the light emitted by the emission means, in the region of the reception means, can only result from its diffraction from red cells.

Other characteristics and advantages of the invention will appear on reading the description which follows.

BRIEF DESCRIPTION OF THE DRAWING

Reference will be made to the appended drawings in which.

DESCRIPTION OF THE PREFERRED EMBODIMENTS

Figure 1:
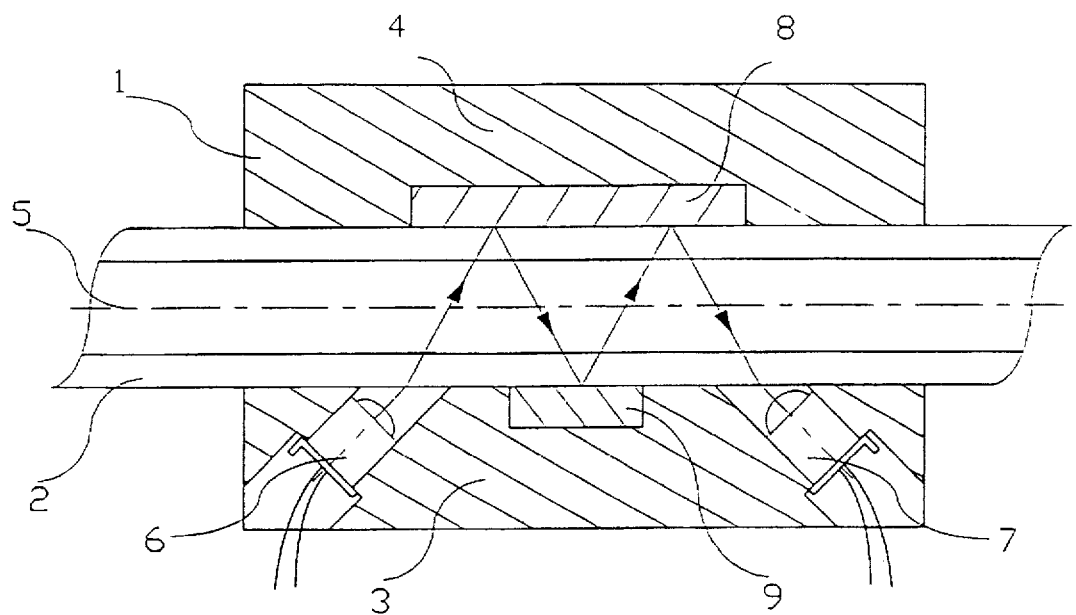
FIG. 1 is a sectional view of a first embodiment of a detection device according to the invention.

The detection device depicted in FIG. 1 comprises a seat 1 formed by a block of plastic comprising an elongate recess of rectangular cross-section configured and sized in order to house and retain a transparent conduit 2 which may, for example, be a portion of a line made of PVC tubing. The seat 1 comprises two zones 3, 4 diametrically opposed to each other with respect to a longitudinal axis 5 of the recess with which axis a longitudinal axis of the line 2 is substantially coincident when the line 2 is engaged in the recess. In a first zone 3 are arranged light emission means 6, such as a light-emitting diode, having a preferential emission direction cutting the longitudinal axis 5 of the recess at 135°, and light reception means 7, such as a phototransistor, having a preferential reception direction cutting the longitudinal axis 5 of the recess at 45°. The diode 6 and the transistor 7 are connected to a signal-processing circuit (not depicted) provided for calculating the attenuation of the light received by the transistor and for comparing the calculated attenuation with ranges of acceptable threshold values. In the second zone 4 are arranged first light deflection means 8, such as a plane mirror, for deflecting in the direction of the first zone 3 at least part of the light emitted by the diode 6.

In accordance with the invention, second light deflection means 9, such as a second plane mirror, are arranged in the first zone 3 in order to deflect, in the direction of the second zone 4, at least part of the light reflected by the first mirror 8 when a line 3 filled with liquid is engaged in the seat 1. The reflective surfaces of the first and second mirrors 8, 9 are parallel to each other and to the longitudinal axis 5 of the recess.

Figure 2:
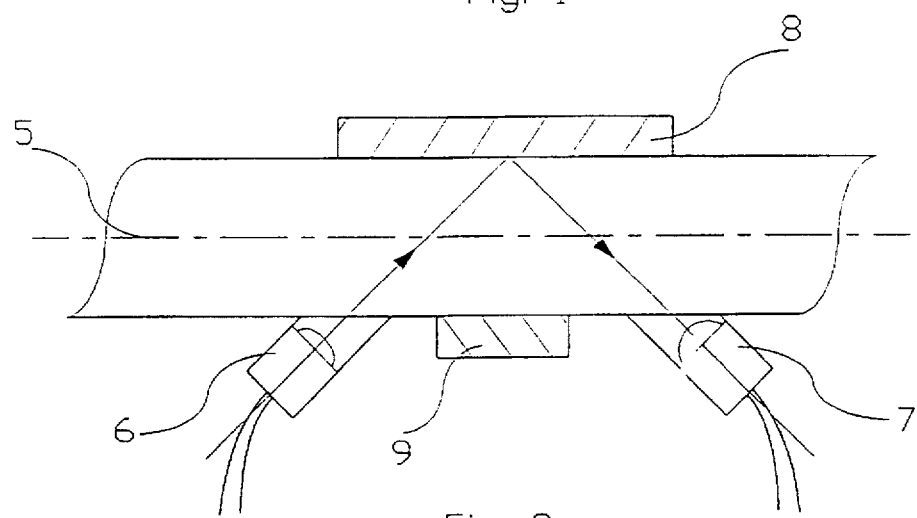
FIGS. 2, 3, 4 illustrate the operation of the device of FIG. 1 in three different detection situations: in the absence of a conduit, in the presence of a conduit filled with gas and in the presence of a conduit filled with liquid.
Figure 3:
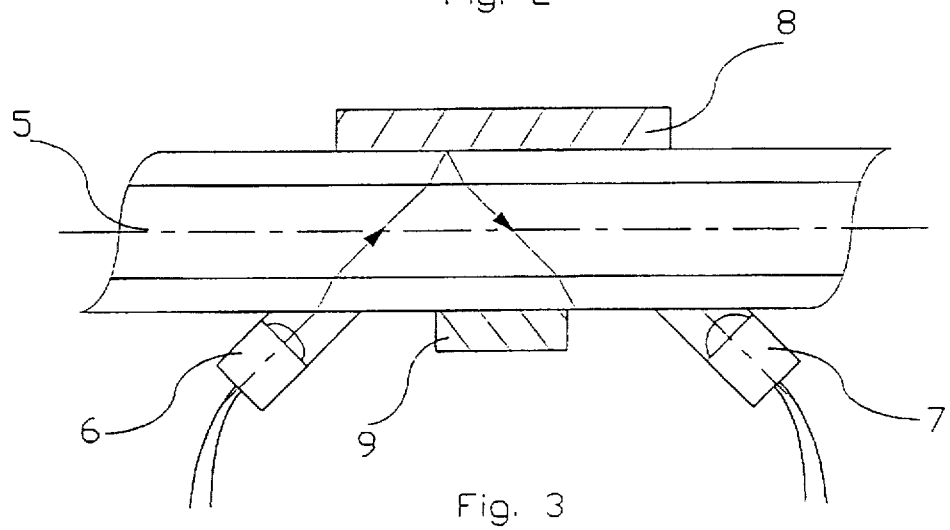
Figure 4:
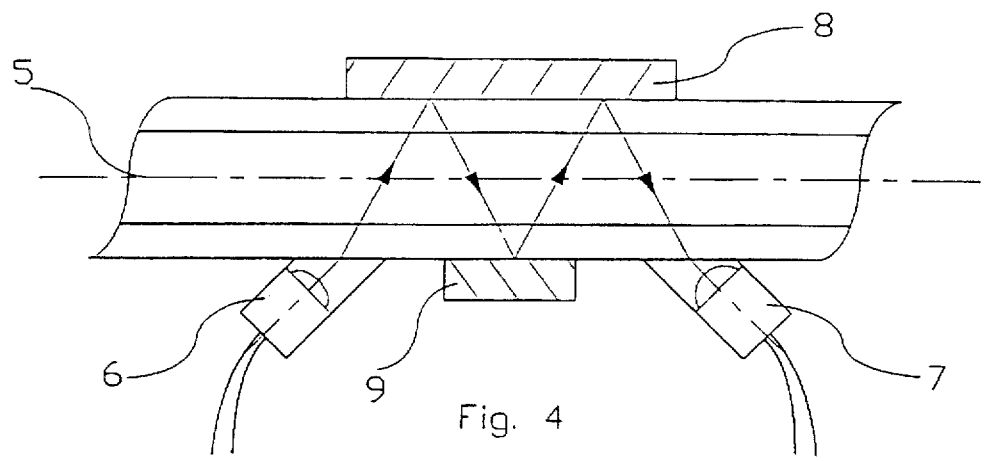

In accordance with the invention, the distance between the diode 6 and the phototransistor 7, as well as the positioning of the mirrors 8, 9 with respect to each other and with respect to the diode 6 and the phototransistor 7, are chosen with consideration for the diameter of the line 2, for the thickness of its walls and for the refractive index of the various optical media through which the light passes, in order that:

in the absence of a line in the seat 1, the light emitted by the diode 6 be deflected, by single reflection from the first mirror 8, in the direction of the phototransistor (see FIG. 2). One of the attractions of this device is that it enables the detector to be calibrated before any use and to take account of the ageing of the diode 6 in the comparisons and calculations carried out by the signal-processing circuit to which the diode 6 and the transistor 7 are connected;

when a line 2 filled with air is engaged in the seat 1, the light emitted by the diode 6 does not reach the diode 7 (see FIG. 3);

when a line 3 filled with liquid is engaged in the seat 1, at least part of the light emitted by the diode 6 is deflected by a triple reflection in the direction of the phototransistor 7, firstly from the first mirror 8, then from the second mirror 9 and finally from the first mirror 8 (see FIGS. 1 and 4).

In FIGS. 1 to 4, the example has been taken of a transparent PVC tubing (index: 1.49) in which a saline solution (index: 1.33) is flowing.

It should be pointed out that, with this device, for each significant detection situation (presence or absence of a line in the seat 1, gas or liquid in the line), there corresponds a different optical path for the light emitted by the diode 6. This characteristic assists in discriminating between the detection situations.

Moreover, the elongation of the optical path for the case in which the line is filled with liquid makes it possible to detect very small concentrations of blood and, moreover, to carry out such a detection in lines of very small diameters. By way of example, the detection device depicted in FIG. 1 makes it possible to detect, in a PVC line of 2.8 millimeter internal diameter and of 4.6 millimeter external diameter in which is flowing, at a flow rate of 58 milliliters/minute, a dialysis liquid mixed with ultrafiltrate, a blood (haematocrit: 35%) outflow having a flow rate of 0.1 milliliters/minute, that is a dilution of 1.7 per thousand.

In the use which has just been mentioned, in order to give the detection device according to the invention a greater selectivity and accuracy, the wavelength of the light emitted by the diode is chosen outside the visible spectrum (in order to prevent interference with ambient light) and outside the spectrum of the wavelengths capable of being absorbed by a liquid having the colour of the blood ultrafiltrate. By way of example, infrared light having a wavelength of approximately 890 nanometers satisfies these conditions.

Figure 5:
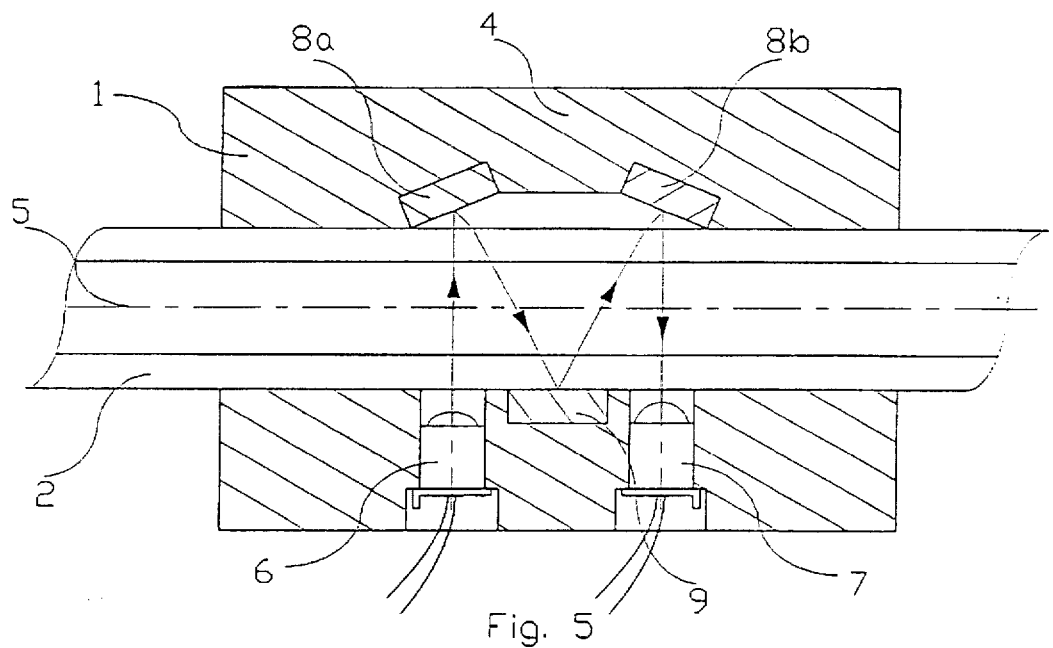
FIG. 5 is a sectional view of a second embodiment of the invention.

FIG. 5 depicts a second embodiment of the invention which is differentiated from that which has just been described in that the preferential emission direction and preferential reception direction of the diode 6 and of the phototransistor 7 are parallel to each other and perpendicular to the longitudinal axis 5 of the recess, and in that the first light deflection means include two mirrors 8a and 8b, the reflective surfaces of which are inclined with respect to the longitudinal axis 5 of the recess so as to be able to reflect respectively at least part of the light emitted by the diode 6 and at least part of the light reflected by the second mirror 9.

With this device, in the absence of a line in the seat 1, at least part of the light emitted by the diode 6 is deflected, by a single reflection from the mirror 8a, towards the phototransistor 7. Moreover, when a line 2 filled with gas is engaged in the seat 1, no light is deflected by the mirrors in the direction of the phototransistor 7. The optical path depicted, which cuts the longitudinal axis 5 of the conduit 2 four times, corresponds to the case in which a line 2 filled with liquid is engaged in the seat 1.

Figure 6:
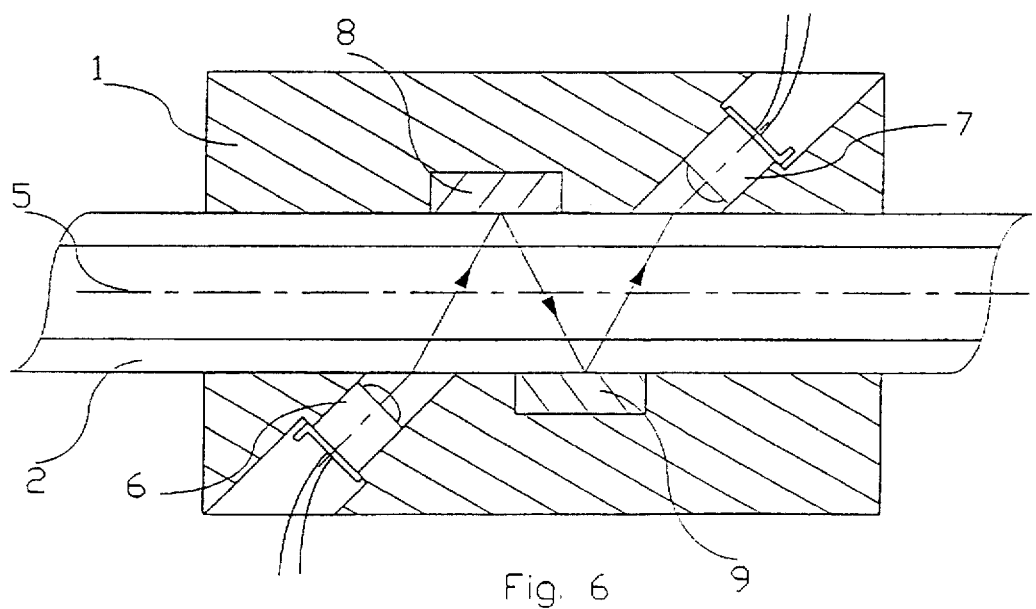
FIG. 6 is a sectional view of a third embodiment of the invention.

In the detection device depicted in FIG. 6, the diode 6 and the phototransistor 7 are respectively arranged in the first zone 3 and in the second zone 4 so that the preferential emission direction of one and the preferential reception direction of the other cut the longitudinal axis 5 of the recess at 45°. As in the device of FIG. 1, the first and second mirrors 8, 9 are parallel to each other and to the longitudinal axis 5 of the recess. The diode 6, the phototransistor 7 and the mirrors 8, 9 are arranged with respect to each other so that, when a line 2 filled with liquid is engaged in the seat 1, at least part of the light emitted by the diode 6 reaches the phototransistor 7 after having passed obliquely through the line 2 three times (optical path depicted in the figure). In the absence of a line in the seat 1 and when a line 2 filled with gas is engaged in the seat 1, no light is deflected by the mirrors 8, 9 in the direction of the phototransistor 7.

The invention is not limited to the embodiments depicted and it is capable of a number of variations. In particular, instead of the mirrors described, the light deflection means could be formed by prisms.

Moreover, although the invention has been described in its application to apparatuses for treating blood by means of extracorporeal circulation, it goes without saying that it can be used in all technical fields in which similar problems are encountered.

I claim:

1. A device for detecting a removable conduit and for determining at least one characteristic of the conduit's contents, the device comprising:

a seat for housing at least one portion of the conduit, the seat including a first and a second zone which are opposite each other with respect to a recess for receiving the conduit;

a light emitter arranged in the first zone and having a preferential light emission direction oriented towards the recess;

a light receptor sensitive to light emitted by the emitter, and having a preferential reception direction oriented towards the recess;

a first light deflector for deflecting, in a direction of the first zone, at least part of the light emitted by the emitter at least when a conduit containing a substantially transparent liquid is engaged in the seat;

a second light deflector for deflecting, in a direction of the second zone, at least part of the light deflected by the first deflector so that, when a conduit containing a substantially transparent liquid is engaged in the seat, at least part of the light emitter by the emitter reaches the receptor after having passed through the conduit at least twice obliquely with respect to a longitudinal axis of the recess; and wherein the emitter, the receptor, the first deflector, and the second deflector are arranged with respect to each other, so that, in the absence of a conduit in the seat, at least part of the light emitted by the emitter reaches the receptor after a single deflection.

2. A device according to claim 1, wherein the receptor has a light-sensitive portion arranged in the first zone, and the emitter, the receptor, the first deflector, and the second deflector are arranged with respect to each other so that, when a conduit containing a substantially transparent liquid is engaged in the seat, at least part of the light emitted by the emission means reaches the receptor after having passed through the conduit four times.

3. A device according to claim 1, wherein the emitter, the receptor, the first deflector and the second deflector are arranged with respect to each other so that, when a conduit containing a gas is engaged in the seat, the receptor receive no light from the emitter.

4. A device according to claim 1, wherein:

the first deflector and the second deflector are plane mirrors having their deflecting surfaces arranged in planes parallel to the longitudinal axis of the recess, the emitter is arranged in order to have a preferential emission direction making an angle of approximately 135° (alternatively 45°) with respect to a longitudinal axis of the recess, and the receptor is arranged in order to have a preferential reception direction making an angle of approximately 45° (alternatively 135°) with respect to the longitudinal axis of the recess.

5. A device according to claim 1, wherein the receptor is arranged in the second zone, and the emitter, the receptor, the first deflector, and the second deflector are arranged with respect to each other so that, when a conduit containing a substantially transparent liquid is engaged in the seat, at least part of the light emitted by the emitter reaches the receptor after having passed through the conduit three times.

6. A device according to any one of claims 1, 2, 3, 4, and 5 for a use as blood detector in a spent-liquid line of an extracorporeal blood treatment apparatus, wherein a wavelength of light emitted by the emitter is chosen to be outside a spectrum of visible light and not to be absorbed by a liquid having a coloration of a blood ultrafiltrate possibly diluted in a saline solution.

7. A device for detecting a removable conduit and for determining at least one characteristic of the conduit's contents, the device comprising:

a seat for housing at least one portion of the conduit, the seat including a first zone, a second zone opposite the first zone, and a recess for receiving the conduit;

a light emitter arranged in the first zone and having a preferential light emission direction oriented towards the recess;

a light receptor sensitive to light emitted by the emitter, and having a preferential reception direction oriented towards the recess;

a first light deflector for deflecting, in a direction of the first zone, at least part of the light emitted by the emitter at least when a conduit containing a substantially transparent liquid is engaged in the seat;

a second light deflector for deflecting, in a direction of the second zone, at least part of the light deflected by the first deflector so that, when a conduit containing a substantially transparent liquid is engaged in the seat, at least part of the light emitted by the emitter reaches the receptor after having passed through the conduit at least twice obliquely with respect to a longitudinal axis of the recess; and wherein the emitter, the receptor, the first deflector, and the second deflector are arranged with respect to each other so that, when a conduit containing a gas is engaged in the seat, the receptor receives no light from the emitter.

8. A device according to claim 7, wherein the receptor has a light-sensitive portion arranged in the first zone, and the emitter, the receptor, the first deflector, and the second deflector are arranged with respect to each other so that, when a conduit containing a substantially transparent liquid is engaged in the seat, at least part of the light emitted by the emission means reaches the receptor after having passed through the conduit four times.

9. A device according to claim 7, wherein the emitter, the receptor, the first deflector and the second deflector are arranged with respect to each other, so that, in the absence of a conduit in the seat, at least part of the light emitted by the emitter reaches the receptor after a single deflection.

10. A device according to claim 7, wherein:

the first deflector and the second deflector are plane mirrors having their deflecting surfaces arranged in planes parallel to the longitudinal axis of the recess, the emitter is arranged in order to have a preferential emission direction making an angle approximately 135° (alternatively 45°) with respect to a longitudinal axis of the recess, and the receptor is arranged in order to have a preferential reception direction making an angle of approximately 45° (alternatively 135°) with respect to the longitudinal axis of the recess.

11. A device according to claim 7, wherein the receptor is arranged in the second zone, and the emitter, the receptor, the first deflector, and the second deflector are arranged with respect to each other so that, when a conduit containing a substantially transparent liquid is engaged in the seat, at least part of the light emitted by the emitter reaches the receptor after having passed through the conduit three times.

12. A device according to any one of claims 7, 8, 9, 10, and 11 for a use as blood detector in a spent-liquid line of an extracorporeal blood treatment apparatus, wherein a wavelength of light emitted by the emitter is chosen to be outside a spectrum of visible light and not to be absorbed by a liquid having a coloration of a blood ultrafiltrate possibly diluted in a saline solution.

* * * * *

UNITED STATES PATENT AND TRADEMARK OFFICE
CERTIFICATE OF CORRECTION

PATENT NO. : 5,644,402
DATED : July 1, 1997
INVENTOR(S) : Jacques CHEVALLET

It is certified that error appears in the above-indentified patent and that said Letters Patent is hereby corrected as shown below:

Claim 1, column 5, line 45, change "light emitter" to --light emitted--.

Claim 3, column 5, line 65, change "receive" to --receives--.

Signed and Sealed this

Twenty-third Day of September, 1997

Attest:

BRUCE LEHMAN

Attesting Officer

Commissioner of Patents and Trademarks